US009297768B2

(12) United States Patent
Yager et al.

(10) Patent No.: US 9,297,768 B2
(45) Date of Patent: Mar. 29, 2016

(54) METHODS AND SYSTEMS FOR LABELING AND DETECTING DEFECTS IN A GRAPHENE LAYER

(71) Applicant: Empire Technology Development LLC, Wilmington, DE (US)

(72) Inventors: Thomas A. Yager, Encinitas, CA (US); Seth Adrian Miller, Englewood, CO (US)

(73) Assignee: Empire Technology Development LLC, Wilmington, DE (US)

( * ) Notice: Subject to any disclaimer, the term of this patent is extended or adjusted under 35 U.S.C. 154(b) by 146 days.

(21) Appl. No.: 14/118,006

(22) PCT Filed: Apr. 18, 2013

(86) PCT No.: PCT/US2013/037175
§ 371 (c)(1),
(2) Date: Nov. 15, 2013

(87) PCT Pub. No.: WO2014/171946
PCT Pub. Date: Oct. 23, 2014

(65) Prior Publication Data
US 2015/0079683 A1    Mar. 19, 2015

(51) Int. Cl.
*G01N 21/64* (2006.01)
*G01N 21/88* (2006.01)
*G01N 21/91* (2006.01)
(Continued)

(52) U.S. Cl.
CPC .............. *G01N 21/88* (2013.01); *C09K 11/06* (2013.01); *G01N 21/64* (2013.01); *G01N 21/77* (2013.01); *G01N 21/8422* (2013.01);
(Continued)

(58) Field of Classification Search
CPC ....................................................... G01N 21/64
USPC ................................. 422/69; 436/5, 166, 169
See application file for complete search history.

(56) References Cited

U.S. PATENT DOCUMENTS 4,372,745 A * 2/1983 Mandle et al. ............... 436/537
5,723,976 A   3/1998 Yoshida et al.
(Continued)

FOREIGN PATENT DOCUMENTS

| CN | 102530929 A | 7/2012 |
| TW | 1326086 B | 6/2010 |
| WO | 9102040 A1 | 2/1991 |

OTHER PUBLICATIONS

Treossi, E. et al, Journal of the American Chemical Society 2009, 131, 15576-15577.*
(Continued)

*Primary Examiner* — Arlen Soderquist
(74) *Attorney, Agent, or Firm* — Moritt Hock & Hamroff LLP; Steven S. Rubin, Esq.

(57) ABSTRACT

Fluorophores or other indicators can be used to label and identify one or more defects in a graphene layer by localizing at the one or more defects and not at other areas of the graphene layer. A substrate having a surface at least partially covered by the graphene layer may be contacted with the fluorophore such that the fluorophore selectively binds with one or more areas of the surface of the underlying substrate exposed by the one or more defects. The one or more defects can be identified by exposing the substrate to radiation. A detected fluorescence response of the fluorophore to the radiation identifies the one or more defects.

24 Claims, 3 Drawing Sheets

(51) Int. Cl.
*G01N 21/77* (2006.01)
*G01N 21/84* (2006.01)
*C09K 11/06* (2006.01)

(52) U.S. Cl.
CPC ....... *G01N 21/91* (2013.01); *C09K 2211/1011* (2013.01); *G01N 2021/8433* (2013.01)

(56) References Cited

U.S. PATENT DOCUMENTS

| | | | |
|---|---|---|---|
| 6,607,918 B2 * | 8/2003 | LaGraff et al. | 436/73 |
| 8,304,242 B2 * | 11/2012 | Zhang | 436/5 |
| 2005/0271808 A1 | 12/2005 | Reust et al. | |
| 2007/0281161 A1 | 12/2007 | Ishida | |
| 2009/0057650 A1 | 3/2009 | Lieber et al. | |
| 2010/0068808 A1 | 3/2010 | Bangera et al. | |
| 2010/0291685 A1 | 11/2010 | Zhang | |
| 2011/0031104 A1 | 2/2011 | Barker et al. | |
| 2011/0117202 A1 | 5/2011 | Bourke, Jr. et al. | |
| 2012/0085991 A1 | 4/2012 | Cohen | |
| 2012/0328906 A1 | 12/2012 | Kwon | |
| 2013/0014977 A1 * | 1/2013 | Chamberlin et al. | 174/257 |
| 2013/0071941 A1 | 3/2013 | Miller | |
| 2014/0154811 A1 * | 6/2014 | Sjong et al. | 436/72 |

OTHER PUBLICATIONS

Kim, J. et al, Journal of the American Chemical Society 2009, 2010, 132, 260-267.*
Kyle, J. R. et al, Nanoscale 2012, 4, 3807-3819.*
Bay, H. H. et al, Materials Research Society Symposium Proceedings 2012, 1451, 51-56.*
Stohr, R. J. et al, ACS Nano 2012, 6, 9175-9181.*
E. Miller et.al., "Fluorescence studies of a silane gel to be applied as a carder in optical sensors", International Journal of Photoenergy, 2005, 46-49, vol. 7.
Ritter, J.E. et al., "Fatigue and Durability of Silane-Bonded Epoxy/Glass Interfaces", The Journal of Adhesion, 2001, 335-351, vol. 76, 4.
International Search Report and Written Opinion for application with application No. PCT/US2013/037175, dated Aug. 9, 2013, 95 pages.

* cited by examiner

METHODS AND SYSTEMS FOR LABELING AND DETECTING DEFECTS IN A GRAPHENE LAYER

CROSS REFERENCE TO RELATED APPLICATION

This application is a U.S. National Stage filing under U.S.C. §371 of International Application No. PCT/US13/37175 filed Apr. 18, 2013, the entirety of which is hereby incorporated by reference.

BACKGROUND

Graphene is a material that generally includes a one atom thick layer of bonded carbon atoms. The carbon atoms are arranged in a regular hexagonal pattern. Graphene has relatively high electrical conductivity and mechanical strength. Graphene may be formed by growing carbon atoms on transitional metal substrates followed by transfer to a final substrate such as silicon dioxide.

SUMMARY

In an embodiment, methods of labeling one or more defects in a graphene layer may comprise providing a substrate having a surface at least partially covered by the graphene layer; and contacting the substrate with an indicator that selectively binds with one or more areas of the surface exposed by the one or more defects in the graphene layer to label the one or more defects.

In an embodiment, systems for labeling one or more defects in a graphene layer may comprise a substrate having a surface at least partially covered by the graphene layer; and a first reservoir containing a solution of an indicator that selectively binds with one or more areas of the surface exposed by one or more defects to label the one or more defects, and configured to contact the substrate with the solution of fluorophore.

In an embodiment, methods of inspecting a graphene layer for one or more defects may comprise providing a substrate having a surface at least partially covered by the graphene layer; contacting the substrate with a fluorophore that selectively binds with one or more areas of the surface exposed by the one or more defects in the graphene layer to label the one or more defects; exposing the substrate to radiation effective to generate a detectable fluorescence response from the fluorophore at the one or more areas of the surface exposed by the one or more defects; and monitoring the fluorescence response of the fluorophore, wherein a detected fluorescence response identifies the one or more defects and an absence of the fluorescence response indicates an absence of the one or more defects.

In an embodiment, systems for inspecting a graphene layer for one or more defects may comprise a substrate having a surface at least partially covered by the graphene layer; a first reservoir containing a solution of fluorophore that selectively binds with one or more areas of the surface exposed by the one or more defects, and configured to contact the substrate with the solution of the fluorophore; a radiation source configured to irradiate the substrate to generate a detectable fluorescence response from the fluorophore at the one or more areas of the surface exposed by the one or more defects; and a detector configured to monitor the fluorescence response of the fluorophore, wherein a detected fluorescence response identifies the one or more defects and an absence of the fluorescence response indicates an absence of the one or more defects.

In an embodiment, kits for labeling one or more defects in a graphene layer on a surface of a substrate may comprise a fluorophore that selectively binds with one or more areas of the surface exposed by the one or more defects in the graphene layer to label the one or more defects; and a set of instructions comprising contacting the substrate with a solution of the fluorophore.

In an embodiment, labeled samples may comprise a substrate having a surface at least partially covered by a graphene layer; and a fluorophore at one or more areas of the surface exposed by one or more defects in the graphene layer to label the one or more defects.

In an embodiment, pretreated samples may comprise a substrate having a surface at least partially covered by a graphene layer; and an amino silane at one or more areas of the surface exposed by one or more defects in the graphene layer to pretreat the one or more areas of the surface for binding with a fluorophore.

DETAILED DESCRIPTION

Figure 1:
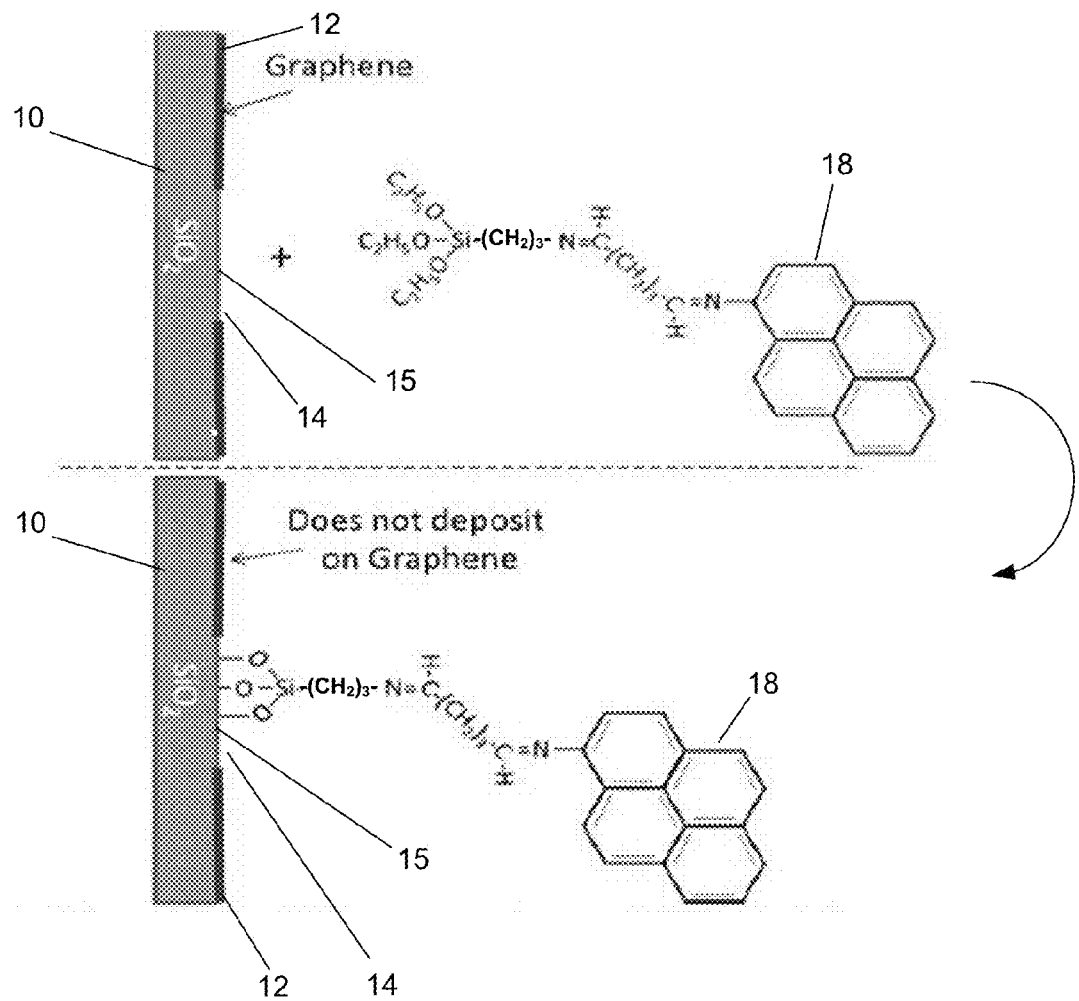
FIG. 1 illustrates labeling of a surface of a substrate exposed by a defect in the graphene layer using a silane fluorophore in accordance with embodiments disclosed herein.

This disclosure is not limited to the particular methods, systems and kits described, as these may vary. The terminology used in the description is for the purpose of describing the particular versions or embodiments only, and is not intended to limit the scope.

Disclosed herein are methods, systems and kits for using fluorophores to label and identify one or more defects in a graphene layer on a surface of a substrate. The fluorophores can localize at the one or more defects by bonding to one or more areas of the surface of the underlying substrate exposed by the one or more defects in the graphene layer. The one or more defects can be identified by exposing the substrate to radiation and detecting a fluorescence response of the fluorophores to the radiation. A detected fluorescence response may identify presence of the one or more defects in the graphene layer. In contrast, an absence of fluorescence response may indicate absence of the one or more defects in the graphene layer.

Methods of Labeling and Identifying Defects in a Graphene Layer

In an embodiment, a method of labeling one or more defects in a graphene layer may include providing a substrate having the graphene layer on the substrate. In some cases, the method of labeling can be used as a quality control test to evaluate a graphene layer for the presence or absence of defects. The labeling may mark locations of the one or more defects with an indicator such as a fluorophore, which can be detected by observing a fluorescence response of the fluorophore to radiation. Other indicators may be a dye, a radioisotope or a quantum dot. The graphene layer may at least partially cover a surface of the substrate, and may have one or more defects that expose one or more areas of the surface of the underlying substrate. The one or more defects may include cracks or voids formed in the graphene layer during production and handling of the graphene layer. The method may further include contacting the substrate with a fluorophore that selectively binds with the one or more areas of the surface exposed by the one or more defects to label the one or more defects. In an embodiment, the substrate may be contacted with a rinsing liquid after contacting the substrate with the fluorophore to remove any non-localized fluorophore from the graphene layer. To identify the defects labeled by the fluorophore, the method may further include exposing the substrate to radiation effective to generate a detectable fluorescence response from the fluorophore at the one or more areas of the surface exposed by the one or more defects, and monitoring the fluorescence response of the fluorophore. A detected fluorescence response may identify the one or more defects, and an absence of the fluorescence response may indicate an absence of the one or more defects in the graphene layer.

In an embodiment, the substrate may be an inorganic polar substrate. As the substrate is a polar substrate, the substrate may have dipole groups adsorbed at the surface, for example, hydroxyl groups. In an embodiment, the substrate may be selected from glass, quartz, silicon dioxide, surface oxidized silicon, transition metal oxides, surface oxidized transition metals, alumina, and a combination thereof.

In an embodiment, the fluorophore can be a silane fluorophore represented by Formula I:

$$C_{16}H_9-N=CH-(CH_2)_X-CH=N-(CH_2)_W-SiV_{(3-Z)}[O(CH_2)_YCH_3]_Z \quad (I)$$

wherein V is —H or —$(CH_2)_UCH_3$, U is an integer of from 0 to 2, W is an integer of from 0 to 3, X is an integer of from 0 to 3, Y is an integer of from 0 to 2, and Z is an integer of from 1 to 3. In an embodiment, the silane fluorophore may be $C_{16}H_9$—N=CH—$(CH_2)_3$—CH=N—$(CH2)_3$-Si$(OCH_2CH_3)_3$. In an embodiment, the silane fluorophore may be formed by contacting a dialdehyde CHO—$(CH_2)_X$—CHO with an aminopyrene $C_{16}H_9$—$NH_2$ to form an aminopyrene derivative fluorophore $C_{16}H_9$—N=CH—$(CH_2)_X$—CHO, and contacting the aminopyrene derivative fluorophore with an amino silane $NH_2$—$(CH_2)_W$—$SiV_{(3-Z)}[O(CH_2)_YCH_3]_Z$ to form the silane fluorophore. The dialdehyde may be selected from glyoxal CHO—CHO, malondialdehyde CHO—$CH_2$—CHO, succindialdehyde CHO—$(CH_2)_2$—CHO, glutaraldehyde CHO—$(CH_2)_3$—CHO, and a combination thereof. The amino silane may be selected from aminotriethoxysilane $NH_2$—Si$[O(CH_2)CH_3]_3$, aminoethyltriethoxysilane NH—$(CH_2)_2$—Si$[O(CH_2)CH_3]_3$, aminopropyltriethoxysilane NH—$(CH_2)_3$—Si$[O(CH_2)CH_3]_3$, aminoethyltrimethoxysilane NH—$(CH_2)_2$—Si$[OCH_3]_3$, aminopropyltrimethoxysilane NH—$(CH_2)_3$—Si$[OCH_3]_3$, aminopropylmethyldiethoxysilane NH—$(CH_2)_3$—Si$(CH_3)[OCH_3]_2$, and a combination thereof. In an embodiment, the dialdehyde may be glutaraldehyde CHO—$(CH_2)_3$—CHO, the aminopyrene derived fluorophore may be $C_{16}H_9$—N=CH—$(CH_2)_3$—CHO, and the amino silane may be aminopropyltriethoxysilane $NH_2$—$(CH_2)_3$—Si$[O(CH_2)CH_3]_3$, as used in the sample Reaction schemes (A) and (B) below.

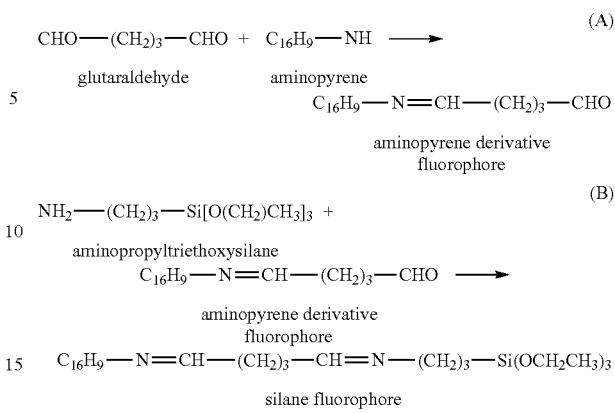

FIG. 1 illustrates the binding of a silane fluorophore 18 to a silicon dioxide substrate 10 as described in the disclosed embodiments. The substrate 10 may have a graphene layer 12 on a surface of the substrate 10. A defect 14 in the graphene layer may expose an area 15 of the surface of the underlying substrate 10. As the silicon dioxide substrate is polar, it can have dipole groups such as hydroxyl groups (not shown) adsorbed at the surface. Without being bound by theory, the silane fluorophore 18 can bind preferentially with the exposed area 15 of the surface and not to the graphene layer 12 due to an amino silane moiety present in the silane fluorophore 18. The alkoxy groups attached to the silicon atom in the amino silane moiety may react with hydroxyl groups (not shown) adsorbed at the surface of the substrate 10 to chemically bind the silane fluorophore 18 to the exposed area 15 of the surface. For example, as shown in FIG. 1, the silane fluorophore 18 can be $C_{16}H_9$—N=CH—$(CH_2)_3$—CH=N—$(CH_2)_3$—Si$(OCH_2CH_3)_3$ which has ethoxy groups in the amino silane moiety. The ethoxy groups can react with the hydroxyl groups adsorbed at the surface of the substrate 10 to bind the silane fluorophore 18 to the exposed area 15 of the surface via an oxygen atom, while forming ethanol (not shown) as a by-product. Accordingly, the silane fluorophore 18 can adhere to the exposed area 15, and not to the graphene layer 12, to label the defect 14 in the graphene layer 12, with a reduced likelihood of leaching from the substrate 10.

In an embodiment, the fluorophore may be an aminopyrene derivative fluorophore represented by formula II:

$$C_{16}H_9-N=CH-(CH_2)_X-CHO \quad (II).$$

Where the fluorophore is the aminopyrene derivative fluorophore, at least the one or more areas of the surface of the substrate exposed by the one or more defects in the graphene layer may include an amino silane having a formula III:

$$NH_2-(CH_2)_W-SiV_{(3-Z)}[O(CH_2)_YCH_3]_Z \quad (III),$$

wherein V is —H or —$(CH_2)_UCH_3$, U is an integer of from 0 to 2, W is an integer of from 0 to 3, X is an integer of from 0 to 3, Y is an integer of from 0 to 2, and Z is an integer of from 1 to 3. In an embodiment, the aminopyrene derivative fluorophore may be $C_{16}H_9$—N=CH—$(CH_2)_3$—CHO, and the amino silane may be aminopropyltriethoxy silane (APTES) $NH_2$—$(CH_2)_3$—Si$[OCH_2CH_3]_3$. The amino silane, as disclosed herein, may bind preferentially with the one or more areas of the substrate surface exposed by the one or more defects in the graphene layer, due to the dipole groups (e.g., hydroxyl groups) adsorbed at the surface of the substrate. In an embodiment, the substrate may be contacted with the amino silane to attach the amino silane to at least the one or more areas of the surface of the underlying substrate exposed by the one or more defects in the graphene layer. The contacting of the substrate with the amino silane may be performed before the substrate contacts with the fluorophore. The aminopyrene derivative fluorophore may then react with the amino silane attached to the substrate, to form a resulting silane fluorophore that chemically binds to the substrate. Accordingly, it will be appreciated that the amino silane can chemically couple the aminopyrene derivative fluorophore to the substrate. In an embodiment, the aminopyrene derivative fluorophore may be formed by contacting a dialdehyde CHO—$(CH_2)_x$—CHO with an aminopyrene $C_{16}H_9$—$NH_2$ to form the aminopyrene derivative fluorophore. The dialdehyde may be selected from glyoxal CHO—CHO, malondialdehyde CHO—$CH_2$—CHO, succindialdehyde CHO—$(CH_2)_2$—CHO, glutaraldehyde CHO—$(CH_2)_3$—CHO, and a combination thereof. In an embodiment, the dialdehyde may be glutaraldehyde CHO—$(CH_2)_3$—CHO and may react with the amino pyrene $C_{16}H_9$—$NH_2$ as described in Reaction scheme (A) above to form aminopyrene derivative fluorophore $C_{16}H_9$—N=CH—$(CH_2)_3$—CHO. The aminopyrene derivative fluorophore may then react with the amino silane attached to the substrate as described in Reaction scheme (B) above.

Figure 2:
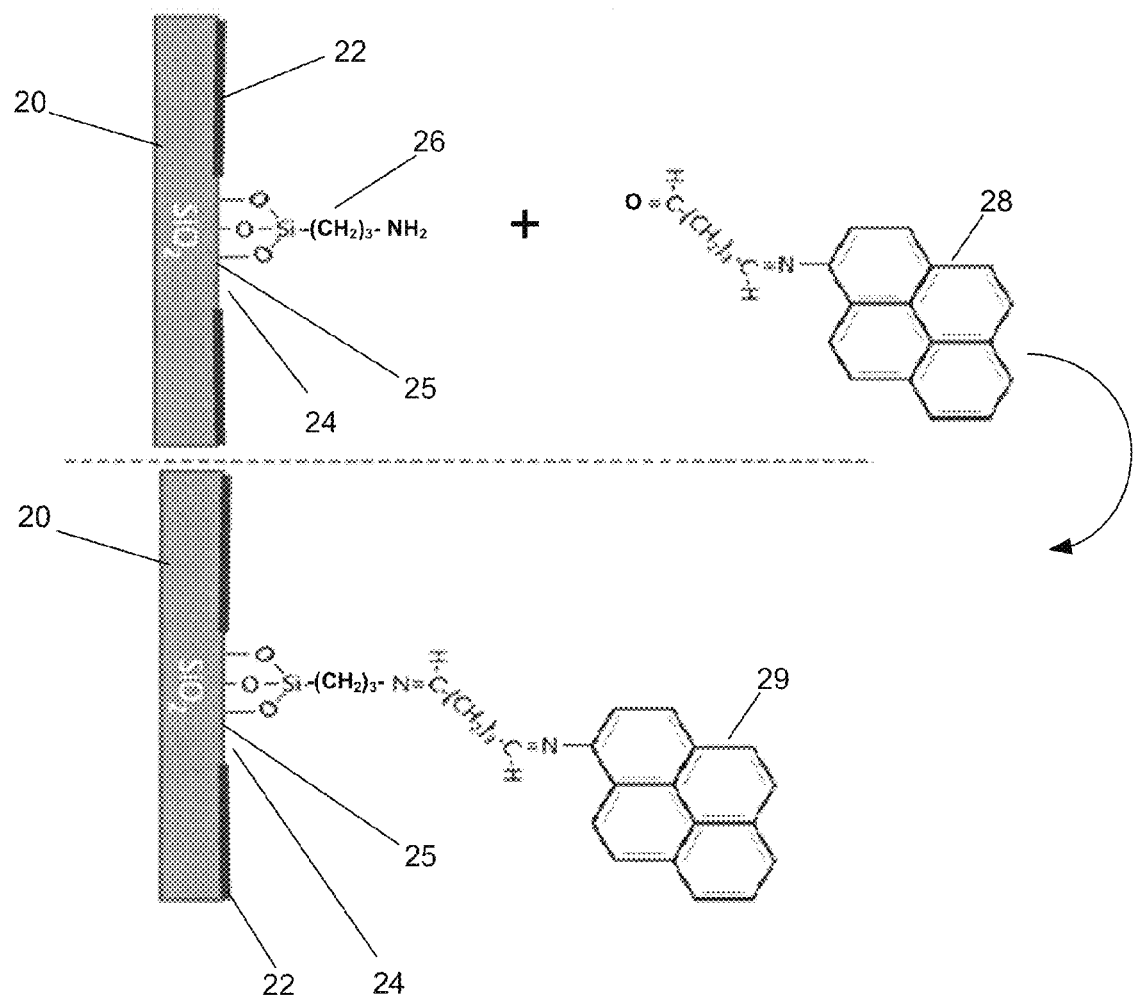
FIG. 2 illustrates labeling of a surface of a substrate exposed by a defect in the graphene layer using an aminopyrene derivative fluorophore in accordance with embodiments disclosed herein.

FIG. 2 illustrates the binding of an aminopyrene derivative fluorophore 28 to a silicon dioxide substrate 20 as described in the disclosed embodiments. The substrate 20 may have a graphene layer 22 on a surface of the substrate 20. A defect 24 in the graphene layer 22 may expose an area 25 of the surface of the underlying substrate 20. The exposed area 25 may have an amino silane 26 attached thereto to result in preferential binding of the amino derivative fluorophore 28 with the area 25 exposed by the defect 24. As disclosed herein, the amino silane can bind with the exposed area 25 of the surface through a reaction between alkoxy groups of the amino silane 26 and hydroxyl groups (not shown) adsorbed at the exposed area 25 of the surface of the substrate 20. The aminopyrene derivative fluorophore 28 may then bind to the amino silane 26 through a reaction between an amine (—$NH_2$) moiety of the amino silane with an aldehyde moiety (—CHO) of the aminopyrene derivative fluorophore 28 to form a resulting silane fluorophore 29. As shown in FIG. 2, an amino derivative silane fluorophore $C_{16}H_9$—N=CHO may chemically bind to an aminopropyltriethoxy silane (APTES) $NH_2$—$(CH_2)_3$—$Si[OCH_2CH_3]_3$ at the surface 25 of the substrate 20 exposed by the defect 24, to form a silane fluorophore $C_{16}H_9$—N=CH—$(CH_2)_3$—CH=N—$(CH_2)_3$—Si$(OCH_2CH_3)_3$. Accordingly, the aminopyrene derivative fluorophore 28 can be chemically coupled to the exposed area 25 and not to the graphene layer 22, via the amino silane 26, to label the defect 24 in the graphene layer 22, with a reduced likelihood of leaching from the substrate 20.

In an embodiment, the contacting of the substrate with the fluorophore may include immersing the substrate into a solution of the fluorophore, providing a solution of the fluorophore on the substrate, or a combination thereof. The solution of fluorophore may include the fluorophore dispersed in a carrier such as toluene, chloroform, or a combination thereof. The providing of the solution of fluorophore on the substrate may include spraying or flowing the solution on the substrate. The contacting of the substrate with the fluorophore may be carried out at a suitable temperature, such as at room temperature, for about 1 to about 10 minutes, or for any length of time sufficient to chemically bind the fluorophore to the substrate. For example, the substrate may be immersed in the solution of fluorophore and left in there for about 1 to about 10 seconds. Alternatively, the solution of fluorophore may be sprayed or flowed onto the substrate continuously for about 1 to about 10 seconds. Where the fluorophore is a silane fluorophore, the concentration of the solution of fluorophore may be about 1 µM to about 1 mM, or any concentration effective to chemically bind the silane fluorophore to the substrate. Where the fluorophore is an aminopyrene derivative fluorophore, the concentration of the solution of fluorophore may be about 1 µM to about 1 mM, or any concentration effective to chemically bind the aminopyrene derivative fluorophore to the amino silane on the substrate.

Where the fluorophore is an aminopyrene derivative fluorophore, before contacting the substrate with the aminopyrene derivative fluorophore, the substrate may be contacted with a solution of amino silane to bind the amino silane with the one or more areas of the surface of the substrate exposed by the one or more defects in the graphene layer. The solution of amino silane may include the amino silane in water/ethanol, water/acetone, or water/isopropanol or a combination thereof. The concentration of the solution of amino silane may be about 0.5 to about 3.0 or any concentration effective to chemically bind the amino silane to the substrate. The amino silane, in accordance with the disclosed embodiments, may chemically couple the aminopyrene derivative fluorophore to the substrate. The contacting of the substrate with the amino silane may include immersing the substrate into a solution of the amino silane, providing a solution of the amino silane on the substrate, or a combination thereof. The providing of the solution of amino silane on the substrate may include spraying or flowing the solution on the substrate. The contacting of the substrate with the amino silane may be carried out at room temperature for about 1 to about 10 minutes. For example, the substrate may be immersed in the solution of amino silane and left in there for about 1 to about 10 minutes. Alternatively, the solution of amino silane may be sprayed or flowed onto the substrate continuously for about 1 to about 10 minutes.

In an embodiment, after contacting the substrate with the fluorophore, the substrate may be contacted with a rinsing liquid to remove any non-localized fluorophore from the graphene layer. The contacting of the substrate with the rinsing liquid can be performed for about 5 to about 30 seconds at room temperature, or until non-localized fluorophore from non-defective areas of the graphene layer are removed. The contacting can be achieved by immersing the substrate into the rinsing liquid, providing the rinsing liquid on the substrate, or a combination thereof. The providing of the rinsing liquid on the substrate may include spraying or flowing the rinsing liquid on the substrate. For example, the substrate may be immersed in the rinsing liquid and left in there for about 5 to about 30 seconds, and may optionally be repeated one or more times to ensure complete removal of the non-localized fluorophores from the graphene layer on the substrate. Alternatively, the rinsing liquid may be sprayed or flowed onto the substrate continuously for about 5 to about 30 seconds. The rinsing liquid may be water, ethanol, acetone, or isopropyl alcohol, or a combination thereof. The sample may be annealed after the rinse at about 100° C., for about 1 to about 10 minutes.

In an embodiment, the exposing of the substrate to radiation may include irradiating the substrate with radiation having a wavelength effective to excite the fluorophore to generate a detectable fluorescence response. The radiation may be produced by a radiation source such as a gas discharge lamp, a light emitting diode, a laser or any source that is capable of producing the radiation. The radiation may be ultraviolet radiation having a wavelength of about 360 nm to about 440 nm. The exposing of the substrate to radiation may be carried out for any suitable duration of time, such as about 1 nanosecond to about 10 seconds.

The fluorescence response can be monitored to determine if the graphene layer has any defects or to determine the locations of the defects. In an embodiment, the monitoring of the fluorescence response of the fluorophore may include monitoring the fluorescence response using a fluorescence microscope, an automated optical inspection machine, multiphoton spectroscopy, scanning laser fluorescence microscopy, photomultiplier tubes, charged-coupled devices, or a combination thereof. A detected fluorescence response can identify the one or more defects, including locations of the one or more defects. An image showing the locations of the one or more defects on the graphene layer may be generated from the detected fluorescence response, for example, by a processor operable to process the fluorescence response. In contrast, if the fluorescence response is absent after exposing the substrate to the radiation, the graphene layer can be understood to not include any defect. The detection can be qualitative or quantitative. The measured graphene layer can be compared against at least one positive control or negative control. One or more positive controls can be used to generate a calibration curve to quantify the number or density of defects in the measured graphene layer.

In an embodiment, the fluorophore may be removed from the substrate after monitoring the fluorescence response. The removal may be achieved by heating the substrate to a temperature effective to decompose the fluorophore, which can then be removed by flowing one or more gases over the substrate. The heating may be carried out for about 5 seconds to about 5 minutes, or any length of time effective to decompose the fluorophore. The one or more gases may be argon, hydrogen or a combination thereof. Where the fluorophore is a silane fluorophore, or an aminopyrene derivative fluorophore that is binded with a substrate pre-treated with amino silane to form a resulting silane fluorophore, the temperature at which the silane fluorophore in both cases may decompose can be about 350° C. Accordingly in an embodiment, the removing of the fluorophore from the substrate may include heating the substrate to about 350° C. to about 400° C. in the presence of one or more flowing gases.

Figure 3:
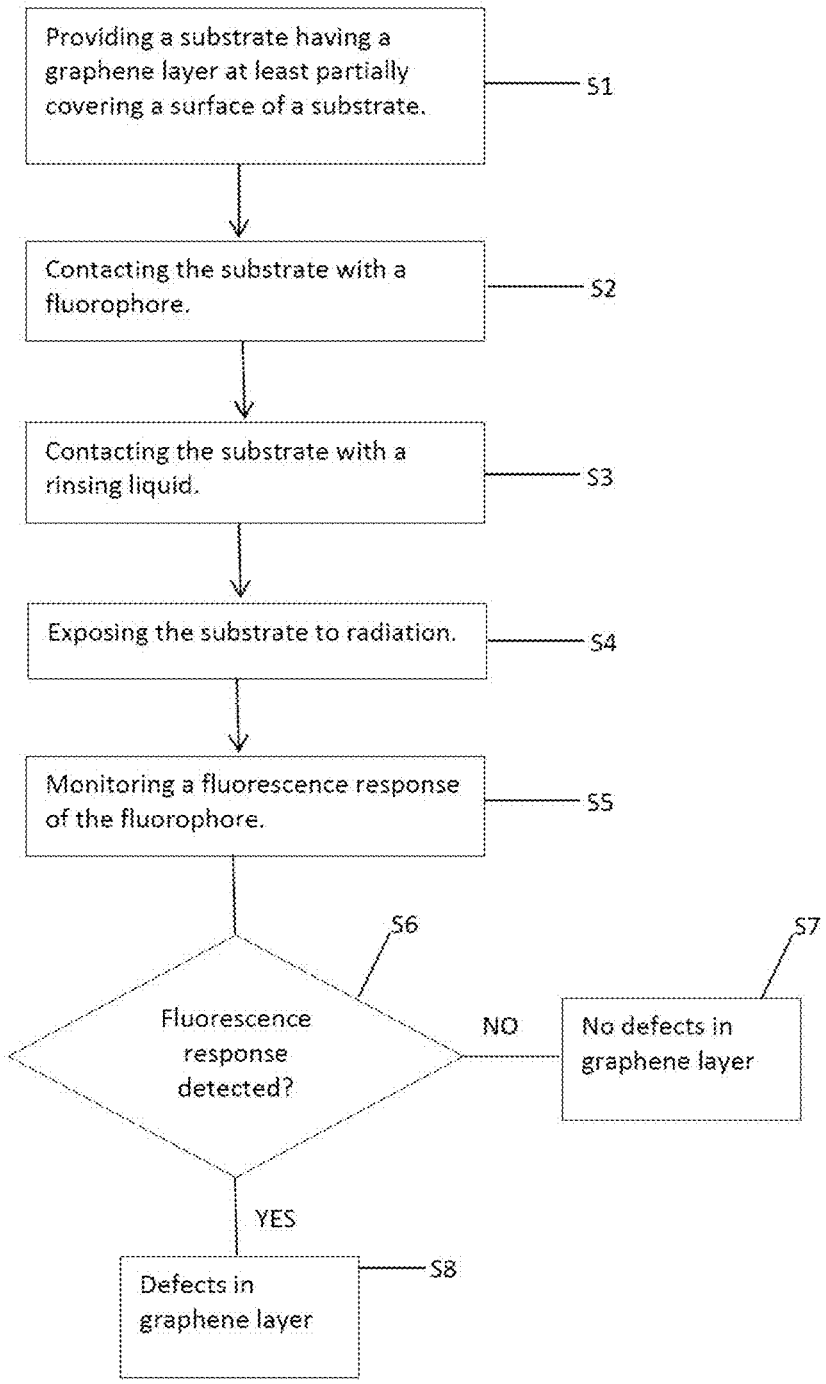
FIG. 3 illustrates a flow diagram of a method of inspecting a graphene layer for one or more defects in accordance with embodiments disclosed herein.

FIG. 3 shows a flow diagram of a method of inspecting a graphene layer for one or more defects in accordance with the disclosed embodiments. Referring to S1, the method may start with providing a substrate having the graphene layer at least partially covering a surface of a substrate. As shown in S2, the method may then include contacting the substrate with a fluorophore that selectively binds with one or more areas of the surface of the substrate exposed by the one or more defects in the graphene layer to label the one or more defects. Next as shown in S3, the method may include contacting the substrate with a rinsing liquid after contacting the substrate with the fluorophore to remove any non-localized fluorophore from the graphene layer. The method may further, as shown in S4, include exposing the substrate to radiation effective to generate a detectable fluorescence response from the fluorophore at the one or more areas of the surface exposed by the one or more defects. Next in S5, the method may include monitoring for a fluorescence response of the fluorophore at the one or more areas of the surface exposed by the one or more defects. As shown in S6, the method may further include determining if a fluorescence response is detected. A detected fluorescence response, as shown in S8, may identify the one or more defects in the graphene layer, confirming the presence of one or more defects in the graphene layer. An absence of the fluorescence response, as shown in S7, may indicate an absence of the one or more defects.

Systems for Labeling and Identifying Defects in a Graphene Layer

A system for labeling one or more defects in a graphene layer may be provided that can implement the methods as described in the disclosed embodiments. The system may include a substrate having a surface at least partially covered by the graphene layer. The graphene layer may have one or more defects that expose one or more areas of the surface of the underlying substrate. Alternatively, the graphene layer may lack such defects.

The system may include a first reservoir that contains a solution of fluorophore. The fluorophore, in accordance with the disclosed embodiments, can selectively bind with the exposed areas of the substrate surface to label the one or more defects. The first reservoir can also be configured to contact the substrate with the solution of fluorophore in accordance with the methods as described in the disclosed embodiments. For example, the first reservoir may be coupled to a valve, which when activated, releases the solution of fluorophore onto the substrate, such as by spraying or flowing the solution on the substrate. Alternatively, the first reservoir may be configured to receive the substrate such that the substrate can be immersed in the first reservoir to contact the substrate with the solution of fluorophore. Accordingly, in an embodiment, a labeled sample may be provided which includes the substrate having a surface at least partially covered by the graphene layer, and the fluorophore binded with the one or more areas of the surface exposed by the one or more defects in the graphene layer to label the one or more defects. The labeled sample may be useful in facilitating identification of the one or more defects in a later of processing as will be described in the disclosed embodiments.

In an embodiment, the system may further include a radiation source configured to irradiate the substrate to generate a detectable fluorescence response from the fluorophore at the one or more areas of the surface of the substrate exposed by the one or more defects in the graphene layer. The radiation source can be a gas-discharge lamp, a light emitting diode, a laser or any source that is capable of producing radiation having a wavelength effective to generate the detectable fluorescence response. In an embodiment, the radiation source may be configured to irradiate the substrate with ultraviolet radiation having a wavelength of about 360 nm to about 440 nm. The system may further include a detector to monitor the fluorescence response of the fluorophore. A detected fluorescence response may identify the one or more defects, including locations of the one or more defects. An absence of the fluorescence response may indicate an absence of the one or more defects. The detector may be a fluorescence microscope, an automated optical inspection machine, or a combination thereof. The detector may also include a processor to process the detected fluorescence response to generate an image showing locations of the one or more defects in the graphene layer. To facilitate the inspection of the graphene layer for defects, the processor may be configured to indicate on a display interface that there are no defects in the graphene layer when the fluorescence response is not detected, and to indicate defects in the graphene layer, for example at locations shown in the generated image, when the fluorescence response is detected. The radiation source and the detector may be a single device or separate devices.

In an embodiment, the system may further include a second reservoir containing a rinsing liquid. The rinsing liquid may, for example, be water, ethanol, or a combination thereof. The second reservoir may be configured to contact the rinsing liquid with the substrate, in accordance with the methods as described in the disclosed embodiments, after the substrate is contacted with the solution of fluorophore to remove any non-localized fluorophore from the graphene layer. For example, the second reservoir may be coupled to a valve, which when activated, releases the rinse liquid onto the substrate such as by spraying or flowing the rinse liquid on the substrate. Alternatively, the second reservoir may be configured to receive the substrate such that the substrate can be immersed in the second reservoir to contact the substrate with the rinsing liquid.

In an embodiment, the substrate may be as described in the disclosed embodiments, and may be an inorganic polar substrate. The substrate may be selected from glass, quartz, silicon dioxide, surface oxidized silicon, transition metal oxides, surface oxidized transition metals, and a combination thereof.

In an embodiment, the fluorophore may be a silane fluorophore or an aminopyrene derivative fluorophore, both as described in the disclosed embodiments. The fluorophore may be provided in solution form where the fluorophore may be dispersed in a suitable carrier. The concentrations of the fluorophore in the carrier, types of suitable carriers and methods of making the fluorophore, are in accordance with the disclosed embodiments.

Where the fluorophore is an aminopyrene derivative fluorophore, the system may further include a third reservoir containing a solution of amino silane that selectively binds with the one or more areas of the surface of the underlying substrate exposed by the one or more defects in the graphene layer. The third reservoir may be configured to contact the amino silane with the substrate before the substrate is contacted with the fluorophore, in accordance with the disclosed embodiments. For example, the third reservoir may be coupled to a valve, which when activated, releases the solution of amino silane onto the substrate such as by spraying or flowing the solution on the substrate. Alternatively, the third reservoir may be configured to receive the substrate such that the substrate can be immersed in the third reservoir to contact the substrate with the amino silane. Accordingly, in an embodiment, a pretreated sample may be provided which includes the substrate having a surface at least partially covered by the graphene layer, and an amino silane binded with the one or more areas of the surface exposed by the one or more defects in the graphene layer. The amino silane in the pretreated sample may chemically couple the fluorophore, for example the aminopyrene derivative fluorophore, to the exposed areas of the substrate where the defects are located.

In an embodiment, the system may further include a heater configured to heat the substrate to a temperature sufficient to remove the fluorophore in an atmosphere of one or more flowing gases. The heater may be configured to carry out the heating after the fluorescence response is monitored. The temperature, types of flowing gases and heating time may be in accordance with the disclosed embodiments.

Also provided herein are systems for implementing the methods of inspecting a graphene layer for one or more defects. Referring to FIG. 3, the steps S1 to S8 may be implemented by the various components of the system as described in the disclosed embodiments.

The elements of the system as described in the disclosed embodiments, such as the first, second, and third reservoirs, the radiation source, the detector, and the heater, may be configured to be in communication with a process controller to implement the methods described in the disclosed embodiments in an automated fashion.

Kits for Labeling and Identifying Defects in a Graphene Layer

A kit for labeling one or more defects in a graphene layer supported on a surface of a substrate may include at least one fluorophore that selectively binds with one or more areas of the surface exposed by the one or more defects to mark the defect, as described in the disclosed embodiments. The kit may also include a set of instructions on using the fluorophore in accordance with the methods described in the disclosed embodiments. In an embodiment, the set of instructions may include contacting the substrate with a solution of the fluorophore.

In an embodiment, the fluorophore in the kit may be a silane fluorophore having a Formula I as described in the disclosed embodiments. The fluorophore may be packaged in solution form where it is dispersed in a carrier at a concentration effective to chemically bind the fluorophore to the substrate. The carriers in which the fluorophore can be dispersed, and amounts of fluorophore in the carrier are as described in the disclosed embodiments. Alternatively, the fluorophore may be packaged separately from the carrier. In some cases, the carrier is provided separately from the kit.

In an embodiment, the fluorophore in the kit may be an aminopyrene derivative fluorophore having the formula II as described in the disclosed embodiments. Where the fluorophore is the aminopyrene derivative fluorophore, the kit may further include an amino silane having the formula III as described in the disclosed embodiments, to chemically couple the aminopyrene derivative fluorophore to the substrate. In an embodiment, the set of instructions accompanying the kit may further include contacting the substrate with a solution of the amino silane before contacting the substrate with the fluorophore, in accordance with the methods described in the disclosed embodiments. The aminopyrene derivative fluorophore and the amino silane may each be packaged in solution form. The carriers in which the aminopyrene derivative fluorophore and the amino silane can be dispersed, and the concentrations of these compounds in the respective carriers, are as described in the disclosed embodiments.

In an embodiment, the kit may further include at least one rinsing liquid, and the set of instructions may further include contacting the substrate with the rinsing liquid after contacting the substrate with the solution of fluorophore. The rinsing liquid may, for example, be water, ethanol, or a combination thereof. The contacting of the substrate with the rinsing liquid may be in accordance with the methods as described in the disclosed embodiments.

The kit may further include items and further instructions relating to identifying the labeled defects. In an embodiment, the set of instructions may further include exposing the substrate to radiation effective to generate a detectable fluorescence response from the fluorophore at the one or more areas of the surface exposed by the defect, and monitoring the fluorescence response of the fluorophore. In accordance with the set of instructions, a detected fluorescence response may identify the one or more defects, including locations of the one or more defects; an absence of the fluorescence response may indicate absence of the one or more defects in the graphene layer. Accordingly, the kit may optionally include a radiation source for generating the detectable fluorescence response from the fluorophore, and a detector for monitoring the fluorescence response. The radiation source and the detector may be as described in the disclosed embodiments. In an embodiment, the set of instructions may further provide guidance on generating an image of the locations of the defects using the detected fluorescence response.

The set of instructions accompanying the kit may further include guidance on removing the fluorophore that is localized at the one or more areas of the surface of the substrate exposed by the one or more defects in the graphene layer, in accordance with the methods of the disclosed embodiments.

It will be appreciated that the methods, systems and kits described in the disclosed embodiments can provide a fast and effective way of checking for defects and/or labeling defects in the graphene layer, thereby improving process control and quality assurance during the production and handling of graphene films. Accordingly, this may be especially beneficial in high volume and/or large area production of graphene films. For example, high speed RAMAN scanning microscopy (HORIBA SCIENTIFIC DUO SCAN IMAGING) may capture an image of 122.5 mm$^2$ in 400 s, and may take 2.7 days to scan a 300 mm wafer. The method of this disclosure may enable high resolution inspection for ten 300 mm wafers per hour.

EXAMPLES

Example 1

Preparation of Aminopyrene Derivative Fluorophore

About 100 mmol of liquid glutaraldehyde CHO—(CH$_2$)$_3$—CHO is added to a 1L of 0.1 mmol solution of aminopyrene C$_{16}$H$_9$—NH$_2$ in toluene at room temperature, to form a solution of aminopyrene derivative fluorophore C$_{16}$H$_9$—N=CH—(CH$_2$)$_3$—CHO in toluene.

Example 2

Preparation of Silane Fluorophore

About 1 mL of 0.1M solution of aminopropyltriethoxysilane (APTES) NH$_2$—(CH$_2$)$_3$—Si[O(CH$_2$)CH$_3$]$_3$ is added to 1 L of the solution of aminopyrene derivative fluorophore from Example 1 at room temperature to form a solution of silane fluorophore C$_{16}$H$_9$—N=CH—(CH$_2$)$_3$—CH=N—(CH$_2$)$_3$—Si(OCH$_2$CH$_3$)$_3$.

Example 3

Silicon Dioxide Substrate with Graphene Layer Lacking Defects

A 5 cm by 5 cm piece of silicon dioxide substrate is coated on one surface with a graphene layer known to be free of surface defects. The substrate is immersed in a first reservoir containing the solution of silane fluorophore from Example 2. The substrate is immersed in the first reservoir for about 1 minute at room temperature and removed. The substrate is then sprayed with water for about 15 seconds to rinse the substrate. The substrate is exposed to ultraviolet radiation of 400 nm produced by a xenon-arc lamp for about 5 seconds. While exposed to the ultraviolet radiation, the substrate is viewed under a fluorescence microscope. It is expected that no fluorescence will be observed on the graphene layer, as the silane fluorophore does not bind to the graphene layer.

Example 4

Labeling of Defects in a Graphene Layer Using a Silane Fluorophore

A 5 cm by 5 cm piece of silicon dioxide substrate is coated on one surface with a graphene layer. Defects in the graphene layer are created by poking the graphene layer at 2 locations, and making 0.5 cm scratch lines in the graphene layer at 2 other locations, with a 34 gauge syringe needle to form "voids" and "cracks". The defects created at the 4 locations expose portions of the underlying surface of the substrate. The substrate is immersed in a first reservoir containing the solution of silane fluorophore from Example 2. The substrate is immersed in the first reservoir for about 1 minute at room temperature and removed. The substrate is then sprayed with water for about 15 seconds to rinse the substrate. The substrate is exposed to ultraviolet radiation of 400 nm produced by a xenon-arc lamp for about 5 seconds. The substrate is then viewed under a fluorescence microscope to monitor a fluorescence response of the silane fluorophore. Fluorescence response is expected to be observed at the 4 locations of the graphene layer where the defects are created, as the silane fluorophore selectively binds to, or localizes at, the portions of the underlying surface of the substrate exposed by the defects, and not the graphene layer. Therefore, the silane fluorophore is expected to label only the defective areas of the graphene layer and not the non-defective areas of the graphene layer, as can be compared with the absence of fluorescence response observed in the non-defective graphene layer in Example 3.

Example 5

Labeling of Defects in a Graphene Layer Using an Aminopyrene Derivative Fluorophore and an Amino Silane A 5 cm by 5 cm piece of silicon dioxide substrate is coated on one surface with a graphene layer. Defects in the graphene layer are created by poking the graphene layer at 2 locations, and making 0.5 cm scratch lines in the graphene layer at 2 other locations, with a 34 gauge syringe needle to form "voids" and "cracks". The defects created at the 4 locations expose portions of the underlying surface of the substrate. The substrate is immersed in a first reservoir containing a 1% solution of aminopropyltriethoxysilane (APTES) NH$_2$—(CH$_2$)$_3$—Si[O(CH$_2$)CH$_3$]$_3$. The substrate is immersed in the first reservoir for about 1 minute at room temperature, and removed. The substrate is immersed in a second reservoir containing the solution of aminopyrene derivative fluorophore from Example 1. The substrate is immersed in the second reservoir for about 1 minute at room temperature, and removed. The substrate is then sprayed with toluene for about 15 seconds to rinse the substrate. The substrate is exposed to ultraviolet radiation of 400 nm produced by a xenon-arc lamp for about 5 seconds. The substrate is then viewed under a fluorescence microscope to monitor a fluorescence response of the aminopyrene derivative fluorophore.

The result is expected to be the same as Example 4. Fluorescence is expected to be observed at the 4 locations of the graphene layer where the defects are created, as the aminopropyltriethoxy silane selectively binds with, or localizes at, the areas of the underlying surface of the substrate exposed by the defects, and not to the graphene layer. Subsequently, the aminopyrene derivative fluorophore may react with the localized aminopropyltriethoxy silane, which chemically couples the fluorophore to the areas of the underlying surface of the substrate exposed by the defects. Therefore, the aminopyrene derivative fluorophore is expected to label only the defective areas of the graphene layer and not the non-defective areas of the graphene layer.

Example 6

Evaluation of a Test Sample Using Positive and Negative Control Samples

A test sample of 5 cm by 5 cm piece of silicon dioxide substrate is coated on one surface with a graphene layer. A set of one negative control sample and five positive control samples are obtained. The negative control sample is known to be free of defects, and the five positive control samples contain known amounts of defects, where each of the five positive control samples contain different amounts of defects. The test sample, negative control sample, and positive control samples are all processed according to the procedure in Example 4. The control sample results are used to prepare a calibration curve. The test sample result is compared against the calibration curve, and is found to be within commercially acceptable limits.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof.

Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method to label one or more defects in a graphene layer, the method comprising:
   providing a substrate having a surface at least partially covered by the graphene layer; and
   contacting the substrate with an indicator that selectively binds with one or more areas of the surface of the substrate exposed by the one or more defects in the graphene layer to label the one or more defects.

2. The method of claim 1, wherein contacting the substrate with the indicator comprises contacting the substrate with an indicator that includes one of a fluorophore, a dye, a radioisotope, or a quantum dot.

3. The method of claim 1, wherein contacting the substrate with the indicator comprises contacting the substrate with an indicator that includes a fluorophore, the method further comprising:
   exposing the substrate to radiation effective to generate a detectable fluorescence response from the fluorophore at the one or more areas of the surface exposed by the one or more defects; and
   monitoring the fluorescence response of the fluorophore, wherein a detected fluorescence response identifies the one or more defects and an absence of the fluorescence response indicates an absence of the one or more defects.

4. The method of claim 3, wherein exposing the substrate to radiation comprises:
   irradiating the substrate with ultraviolet radiation having a wavelength of about 360 nm to about 440 nm.

5. The method of claim 3, further comprising:
   removing the fluorophore from the one or more areas of the surface exposed by the one or more defects.

6. The method of claim 1, further comprising contacting the substrate with a rinse liquid one or more times after contacting the substrate with the indicator to remove any non-localized indicator from the graphene layer.

7. The method of claim 1, wherein providing the substrate comprises providing a substrate that includes an inorganic polar substrate.

8. The method of claim 1, wherein contacting the substrate with the indicator comprises contacting the substrate with an indicator that includes a fluorophore and the fluorophore includes a silane fluorophore having a Formula I:

$$C_{16}H_9-N=CH-(CH_2)_X-CH=N-(CH_2)_W-SiV_{(3-Z)}[O(CH_2)_YCH_3]_Z \quad (I)$$

wherein V is —H or —$(CH_2)_UCH_3$, U is an integer of from 0 to 2, W is an integer of from 0 to 3, X is an integer of from 0 to 3, Y is an integer of from 0 to 2, and Z is an integer of from 1 to 3.

9. The method of claim 8, wherein the silane fluorophore includes $C_{16}H_9-N=CH-(CH_2)_3-CH=N-(CH_2)_3-Si(OCH_2CH_3)_3$.

10. The method of claim 1, wherein contacting the substrate with the indicator comprises contacting the substrate with an indicator that includes a fluorophore and the fluorophore includes an aminopyrene derived fluorophore having a formula II:

$$C_{16}H_9-N=CH-(CH_2)_X-CHO \quad (II);$$

and at least the one or more areas of the surface exposed by the one or more defects comprise an amino silane having a formula III:

$$NH_2-(CH_2)_W-SiV_{(3-Z)}[O(CH_2)_YCH_3]_Z \quad (III),$$

wherein V is —H or —$(CH_2)_UCH_3$, U is an integer of from 0 to 2, W is an integer of from 0 to 3, X is an integer of from 0 to 3, Y is an integer of from 0 to 2, and Z is an integer of from 1 to 3.

11. The method of claim 10, further comprising contacting the substrate with the amino silane before contacting the substrate with the indicator that includes the fluorophore, the amino silane at least binding with the one or more areas of the surface exposed by the one or more defects.

12. The method of claim 10, wherein the aminopyrene derived fluorophore includes $C_{16}H_9-N=CH-(CH_2)_3-CHO$, and the amino silane includes aminopropyltriethoxysilane $NH-(CH_2)_3-Si[O(CH_2)CH_3]_3$.

13. A system to label one or more defects in a graphene layer, the system comprising:
   a substrate having a surface at least partially covered by the graphene layer; and
   a first reservoir that contains a solution of an indicator that selectively binds with one or more areas of the surface of the substrate exposed by one or more defects to label the one or more defects in the graphene layer, and configured to contact the substrate with the solution of the indicator.

14. The system of claim 13 wherein the indicator includes a fluorophore, the system further comprising:
   a radiation source configured to irradiate the substrate to generate a detectable fluorescence response from the fluorophore at the one or more areas of the surface exposed by the one or more defects; and
   a detector to monitor the fluorescence response of the fluorophore, wherein a detected fluorescence response identifies the one or more defects and an absence of the fluorescence response indicates an absence of the one or more defects.

15. The system of claim 13, wherein the indicator includes a fluorophore and the fluorophore includes a silane fluorophore having a Formula I:

$$C_{16}H_9-N=CH-(CH_2)_X-CH=N-(CH_2)_W-SiV_{(3-Z)}[O(CH_2)_YCH_3]_Z \quad (I)$$

wherein V is —H or —$(CH_2)_UCH_3$, U is an integer of from 0 to 2, W is an integer of from 0 to 3, X is an integer of from 0 to 3, Y is an integer of from 0 to 2, and Z is an integer of from 1 to 3.

16. The system of claim 15, wherein the silane fluorophore includes $C_{16}H_9-N=CH-(CH_2)_3-CH=NSi(OCH_2CH_3)_3$ or $C_{16}H_9-N=CH-(CH_2)_3-CH=N-(CH_2)_3-Si(OCH_2CH_3)_3$.

17. The system of claim 14, wherein the radiation source is configured to provide ultraviolet radiation having a wavelength of about 360 nm to about 440 nm.

18. The system of claim 14, further comprising a heater configured to heat the substrate to a temperature sufficient to remove the fluorophore from the one or more areas of the surface of the substrate exposed by the one or more defects.

19. The system of claim 18, wherein the heater is configured to heat the substrate to about 350° C. to about 400° C. in presence of one or more flowing gases.

20. The system of claim 13, wherein the indicator includes a fluorophore and the fluorophore includes an aminopyrene derived fluorophore having a formula II:

$$C_{16}H_9-N=CH-(CH_2)_X-CHO \quad (II);$$

and at least the one or more areas of the surface exposed by the one or more defects comprise an amino silane having a formula III:

$$NH_2-(CH_2)_W-SiV_{(3-Z)}[O(CH_2)_Y CH_3]_Z \quad (III),$$

wherein V is —H or —$(CH_2)_U CH_3$, U is an integer of from 0 to 2, W is an integer of from 0 to 3, X is an integer of from 0 to 3, Y is an integer of from 0 to 2, and Z is an integer of from 1 to 3.

21. The system of claim 20, further comprising a second reservoir that contains a solution of the amino silane that selectively binds with the one or more areas of the surface exposed by the one or more defects, and configured to contact the amino silane with the substrate before the substrate is contacted with the fluorophore.

22. The system of claim 20, wherein the aminopyrene derived fluorophore includes $C_{16}H_9$—N=CH—$(CH_2)_3$—CHO, and the amino silane includes aminopropyltriethoxysilane $NH_2$—$(CH_2)_3$—Si[O$(CH_2)CH_3]_3$.

23. A method to inspect a graphene layer for one or more defects, the method comprising:
   providing an inorganic polar substrate having a surface at least partially covered by the graphene layer;
   contacting the substrate with a fluorophore that selectively binds with one or more areas of the surface of the substrate exposed by the one or more defects in the graphene layer to label locations of the one or more defects;
   exposing the substrate to radiation effective to generate a detectable fluorescence response from the fluorophore at the one or more areas of the surface of the substrate exposed by the one or more defects; and
   monitoring the fluorescence response of the fluorophore, wherein a detected fluorescence response identifies the one or more defects and an absence of the fluorescence response indicates an absence of the one or more defects.

24. The method of claim 23, further comprising contacting the substrate with a rinse liquid one or more times after contacting the substrate with the fluorophore to remove any non-localized fluorophore from the graphene layer.

* * * * *